United States Patent
Hajek

(10) Patent No.: US 8,490,220 B1
(45) Date of Patent: Jul. 23, 2013

(54) FEMALE URINATION ASSISTANCE DEVICE

(76) Inventor: Anne C. Hajek, Sioux Falls, SD (US)

( * ) Notice: Subject to any disclaimer, the term of this patent is extended or adjusted under 35 U.S.C. 154(b) by 513 days.

(21) Appl. No.: 12/850,381

(22) Filed: Aug. 4, 2010

(51) Int. Cl.
A47K 11/00 (2006.01)

(52) U.S. Cl.
USPC .......................................................... 4/144.4

(58) Field of Classification Search
USPC ................................. 4/144.1–144.4
See application file for complete search history.

(56) References Cited

U.S. PATENT DOCUMENTS

| | | | |
|---|---|---|---|
| 3,964,111 A | | 6/1976 | Packer |
| 4,500,314 A | * | 2/1985 | Brendling ...................... 604/346 |
| 4,531,245 A | * | 7/1985 | Lowd et al. .................... 4/144.3 |
| 4,771,484 A | | 9/1988 | Mozell |
| 5,091,998 A | | 3/1992 | Witzke |
| D335,924 S | * | 5/1993 | Nilsson ........................ D24/122 |
| 5,370,637 A | | 12/1994 | Brodeur |
| 5,893,176 A | | 4/1999 | Magiera |
| 6,434,757 B1 | | 8/2002 | Filsouf |
| 6,547,771 B2 | | 4/2003 | Robertson |
| 6,719,741 B2 | | 4/2004 | Ching |
| 7,325,256 B1 | * | 2/2008 | Pecinka, Sr. et al. .......... 4/144.1 |
| 2007/0006368 A1 | | 1/2007 | Key |
| 2009/0048569 A1 | | 2/2009 | Salehi |

OTHER PUBLICATIONS

"Sani-Fem Freshette Feminine Urinary Director", www.rei.com/product/407267.

* cited by examiner

Primary Examiner — Huyen Le
(74) Attorney, Agent, or Firm — Jeffrey A. Proehl; Woods, Fuller, Shultz & Smith, P.C.

(57) ABSTRACT

A urination assistance device comprises an upper body interface portion defining a collection opening, and a medial flow-through portion mounted on the body interface element and defining a passage therethrough. The flow-through portion has opposite ends with opposite openings, and the passage is in fluid communication with the collection opening of the body interface portion. A lower exit portion is mounted on the flow-through portion and defines an exit opening for providing a hand hold for a user to grasp to extend the flow-through portion and establish a direction of urine exit from the device. In some embodiments, one portion selected from the body interface portion and the exit portion is receivable in another portion selected from the body interface portion and the exit portion, with the flow-through portion positioned between the one portion and the another portion. In some embodiments, the inner rim is substantially circular in shape.

20 Claims, 6 Drawing Sheets

FEMALE URINATION ASSISTANCE DEVICE

BACKGROUND

1. Field

The present disclosure relates to female urination aids and more particularly pertains to a new female urination assistance device for permitting females to pass urine while standing in an easily guidable manner while providing compact transport of the device before use, as well as convenient disposal after a single use.

2. Description of the Prior Art

Various device and apparatus have been devised for the purpose of assisting females in urinating when it is inconvenient, undesirable or just impossible to be seated. The designs of the known devices are believed to be less than optimal. Many if not all of the designs are intended to mirror the shape of the female anatomy adjacent to the urethra. Also, many if not all of the designs are intended and constructed for repeated use.

SUMMARY

In view of the foregoing disadvantages inherent in the known types of female urination aids now present in the prior art, the present disclosure describes a new female urination assistance device which may be utilized for permitting females to pass urine while standing in an easily guidable manner while providing compact transport of the device before use, as well as convenient disposal after a single use.

In one aspect, the present disclosure relates to a urination assistance device for guiding urine flow from the human body. The device may comprise an upper body interface portion defining a collection opening, and a medial flow-through portion mounted on the body interface element and defining a passage therethrough. The flow-through portion has opposite ends with opposite openings and being elongated between the ends. The passage is in fluid communication with the collection opening of the body interface portion. A lower exit portion may be mounted on the flow-through portion and define an exit opening for exit of urine moving through the passage of the flow-through portion for providing a hand hold for a user to grasp to extend the flow-through portion and establish a direction of urine exit from the device. One portion selected from the body interface portion and the exit portion is receivable in another portion selected from the body interface portion and the exit portion, with the flow-through portion positioned between the one portion and the another portion.

In another aspect, the present disclosure relates to a urination assistance device for guiding urine flow from the human body. The device may comprise an upper body interface portion defining a collection opening. The body interface portion includes an annular interface element having a raised inner rim positioned adjacent to the collection opening. The inner rim is substantially circular in shape. An outer flange extends radially outwardly from the inner rim and has an upper flange surface depressed with respect to an upper edge surface of the inner rim. A medial flow-through portion may be mounted on the body interface element and may define a passage therethrough. The flow-through portion has opposite ends with opposite openings and being elongated between the ends. The passage is in fluid communication with the collection opening of the body interface portion. A lower exit portion defines an exit opening for exit of urine moving through the passage of the flow-through portion and provides a hand hold for a user to grasp to extend the flow-through portion and establish a direction of urine exit from the device.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein.

DETAILED DESCRIPTION

Figure 1:
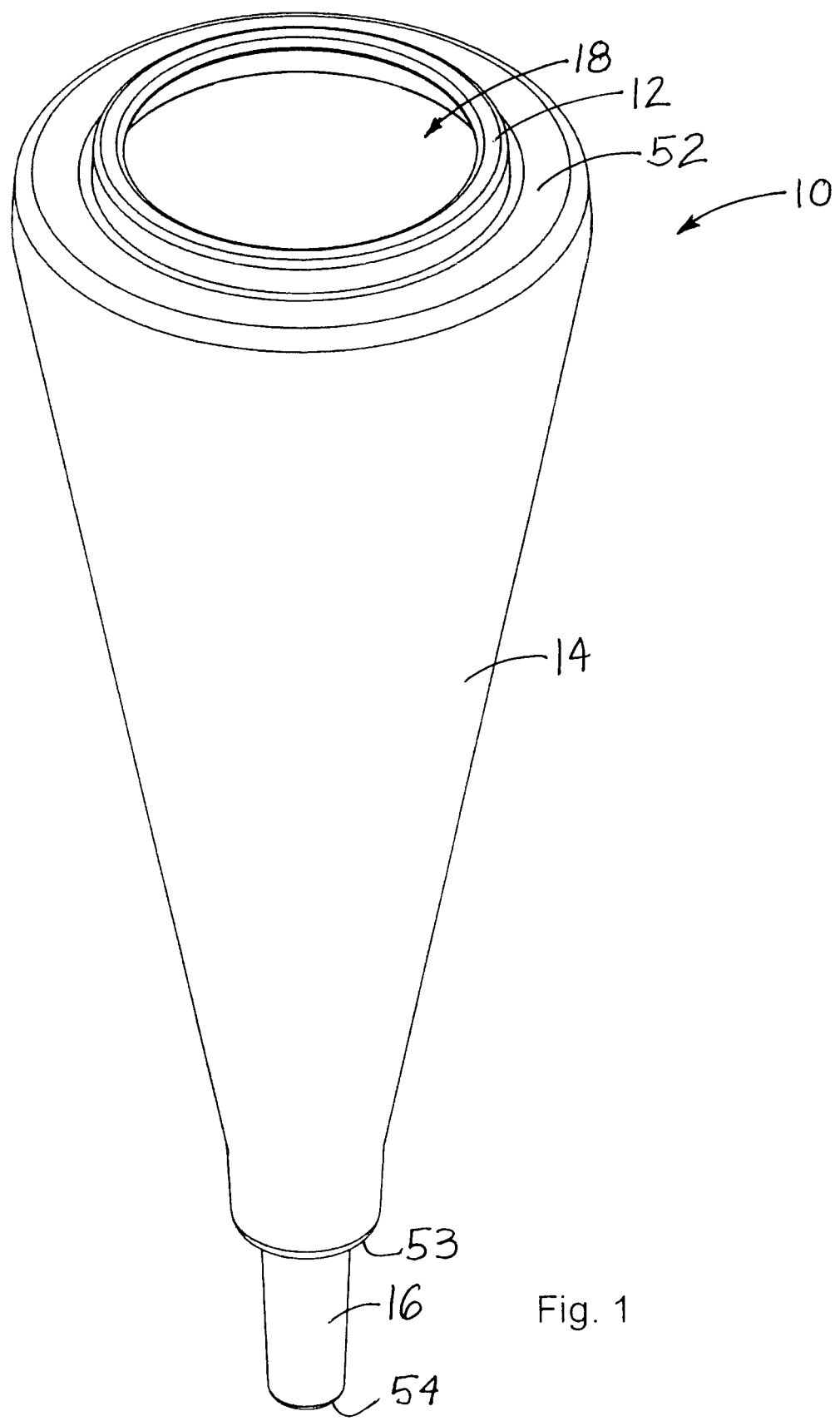
FIG. 1 is a schematic perspective view of a new female urination assistance device according to the present disclosure.
Figure 2:
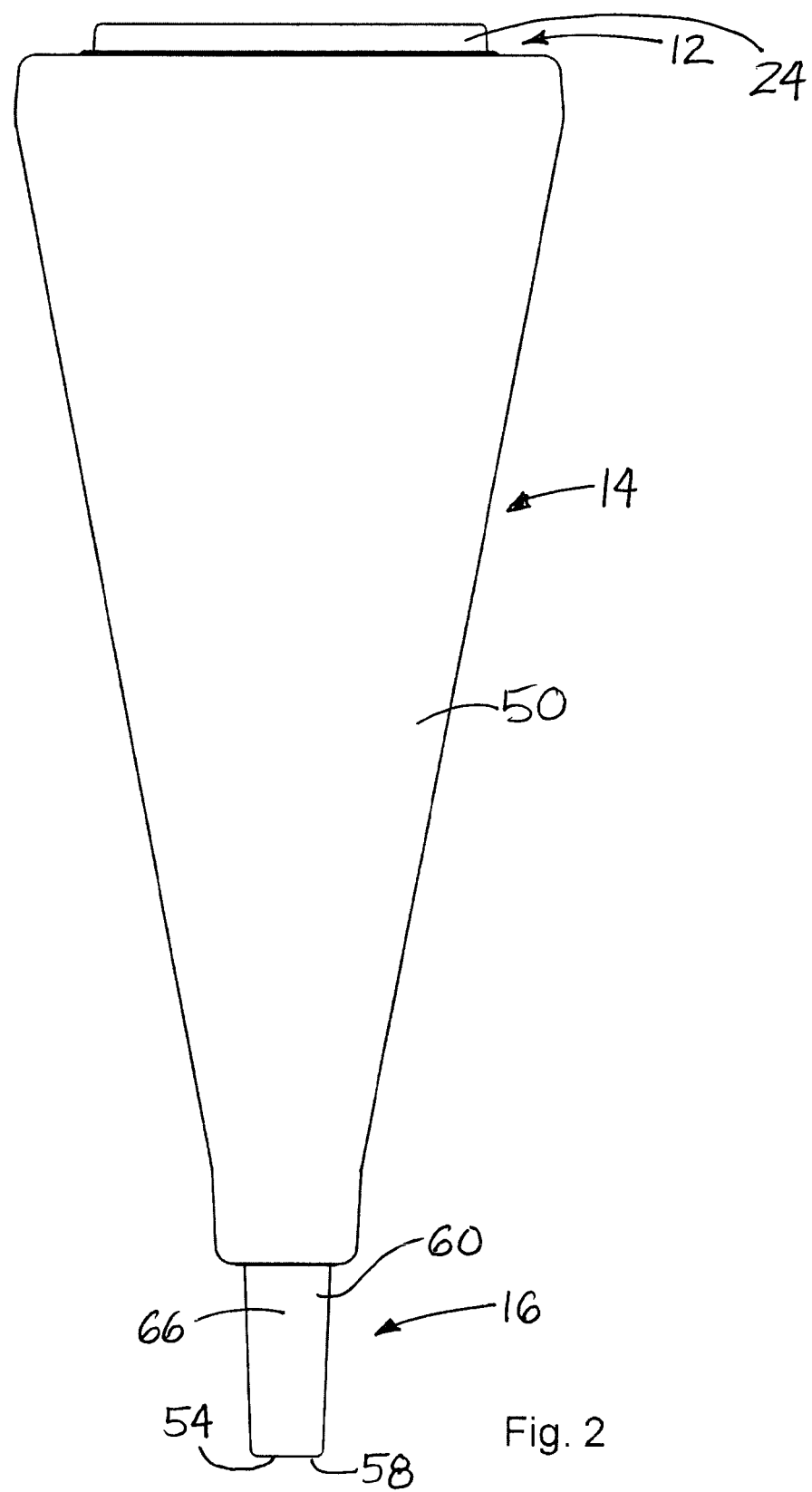
FIG. 2 is a schematic side view of the device, according to an illustrative embodiment.
Figure 3:
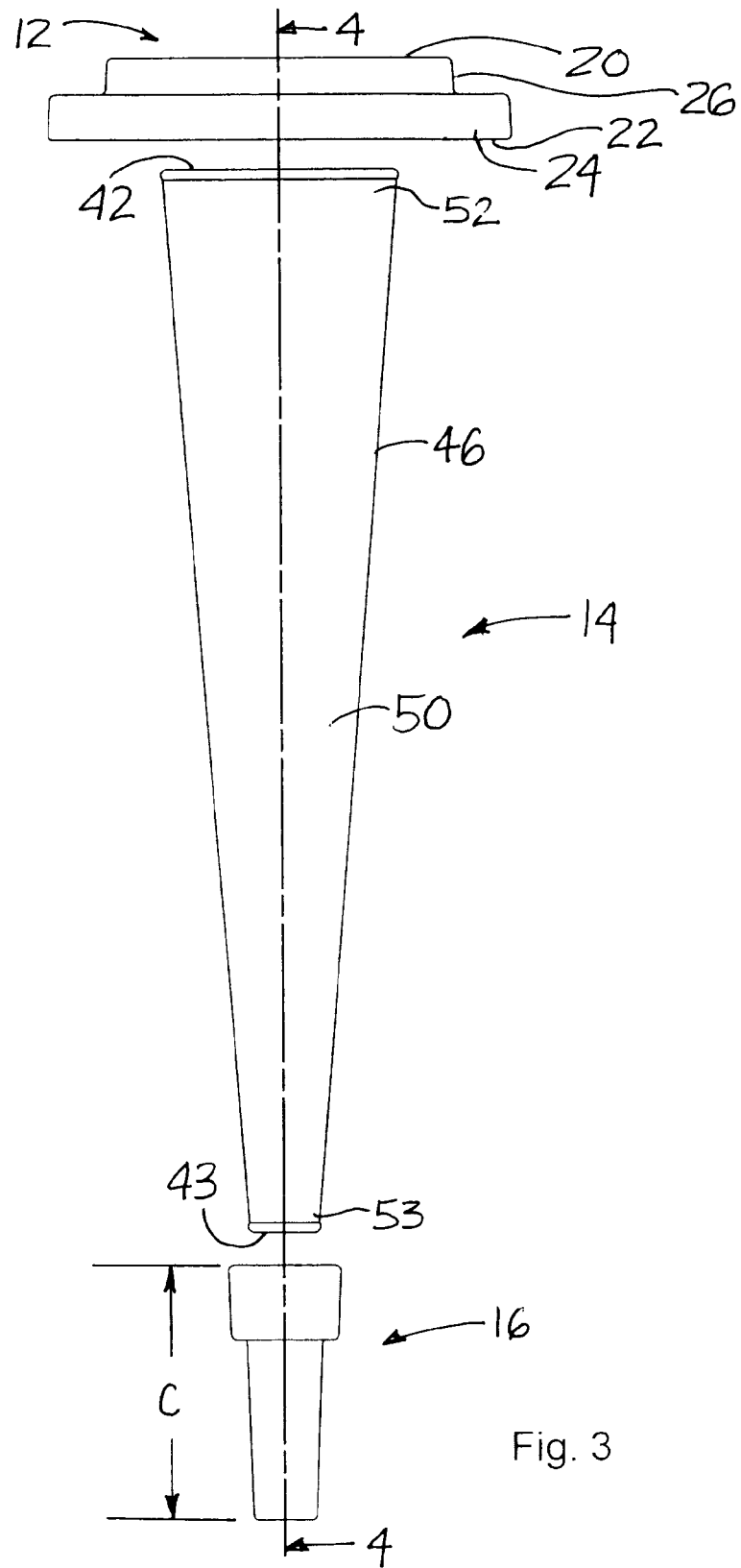
FIG. 3 is a schematic side view of the elements of the device in an exploded relationship.
Figure 4:
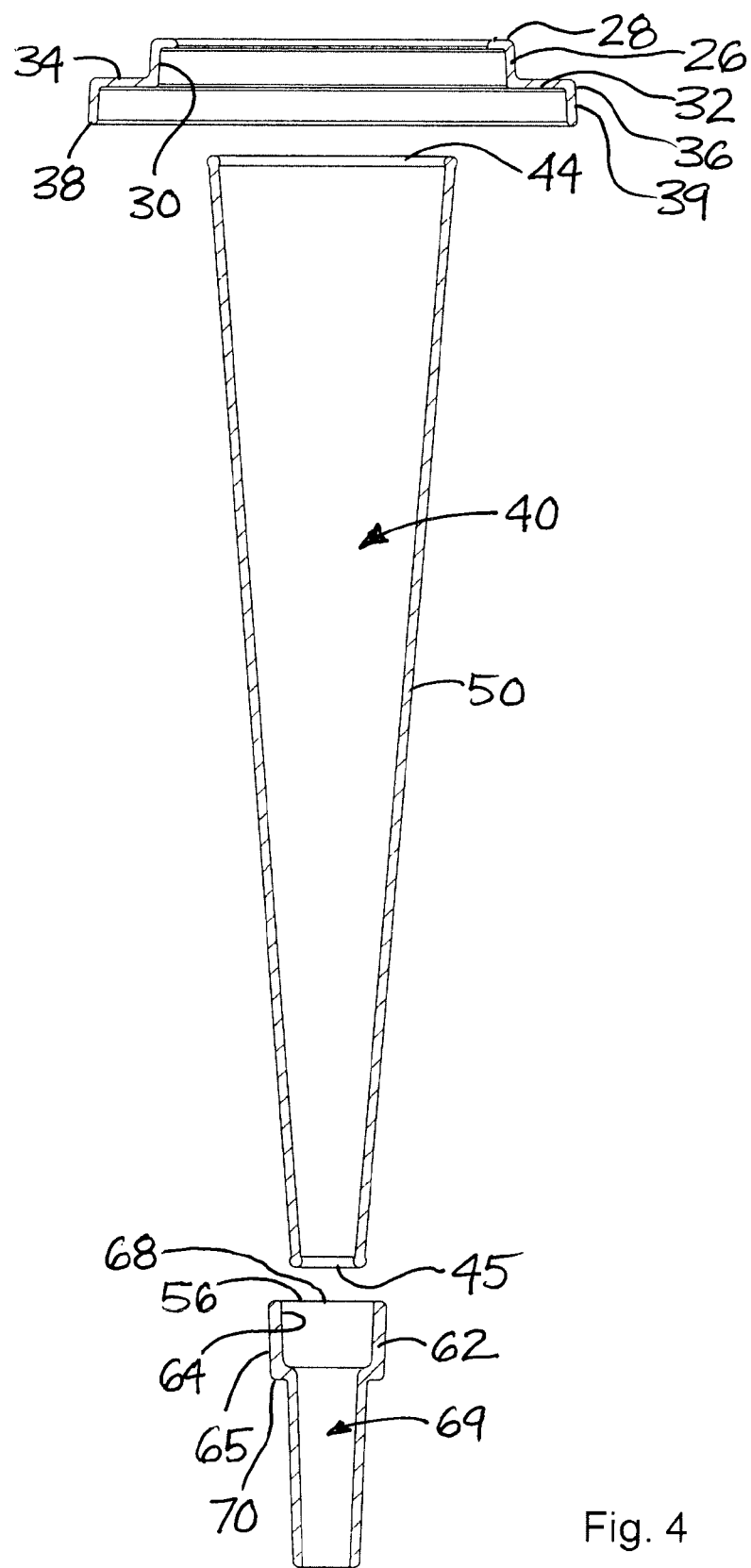
FIG. 4 is a schematic side sectional view of the exploded elements of the device taken along line 4-4 of FIG. 3.

With reference now to the drawings, and in particular to FIGS. 1 through 7 thereof, a new female urination assistance device embodying the principles and concepts of the disclosed subject matter will be described.

Applicant has recognized that the known female urination aids have a number of drawbacks, including the intention to provide reusable devices that are accordingly constructed to provide some degree of durability. This intention has led to devices that are bulkier than necessary to stand up to repeated use. Applicant discloses in this specification a device with embodiments that are structured to be more compact and therefore easier to transport in a more discreet manner, as well as being easier to use as a result of the smaller size. The embodiments are also suitable for disposal after a single use, which avoids any concern for durability or cleanup, and provides a more sanitary option.

Further, applicants have recognized that the attempts to design devices that are shaped to mirror the shape of the female anatomy in the pubic area have resulted in devices that are bulkier than truly necessary to be functional and, perhaps more significantly, have resulted in devices that in actuality are not as effective in locating and providing a reliable seal between the devices and the female anatomy when being used. Applicants have determined that, in general, a device having a shape that is substantially round or circular at the interface with the body can be easier to use and more effective than devices that are designed to mimic or complement the female anatomy.

In general, this disclosure regards a urination assistance device 10 for guiding urine flow from the human body, particularly (but not necessarily) a female body when she is standing. The device 10 in a general sense may include a body interface portion 12, a flow-through portion 14, and an exit portion 16. When oriented for use by a user, the body interface portion 12 may comprise an upper portion, the flow-through portion 14 may comprise a medial or middle portion, and the exit portion 16 may comprise a lower portion, and these portions may be referred to as such in the description.

In greater detail, the body interface portion 12 may define a collection opening 18, and may generally have a top 20 and a bottom 22. The body interface portion 12 may have a substantially rigid and stiff character, and therefore may be formed of a substantially rigid material providing such characteristics. The rigidity of the body interface portion 12, and the material forming the portion 12, may make the portion 12 substantially inflexible, particularly when the portion 12 is pressed by the fingers of the user against the soft flesh of the body. The body interface portion 12 may be formed of a single piece of material, such as from a plastic material having suitable characteristics or constructed so as to gain the desired characteristics.

The body interface portion 12 may comprise an annular interface element 24 or member which may form the collection opening 18 which may have a first diameter A. The interface element 24 may include a raised inner rim 26 that is positioned substantially directly adjacent to the collection opening 18, and may define the collection opening. The inner rim 26 may be, and preferably is, substantially circular in shape, and so may be the collection opening. In some embodiments, the shape of the inner rim may not be perfectly circular, but variation in the measurement across the rim 26 at different locations on the rim may be up to approximately 20 percent. The raised inner rim 26 may have an upper edge 28 which is a relatively thin surface extending about the collection opening. The inner rim 26 may also have an inner annular surface 30 which may be substantially cylindrical in shape, and the inner annular surface 30 may have a second diameter B.

The interface element 24 may also include an outer flange 32 that extends radially outwardly from the inner rim 26, and may have an upper flange surface 34 that is depressed with respect to the surface of the upper edge 28. The upper flange surface 34 may be relatively wider in a radial direction than the surface of the upper edge 28 of the inner rim. The outer flange 32 has an outer perimeter 36 which may be substantially circular in shape, and may be formed by an outer perimeter edge 38.

In the illustrative embodiment, the interface element may be formed by a stepped wall of substantially uniform thickness, with an outer perimeter skirt section 39 located adjacent to the outer perimeter edge 38. Further, a rim extension 27 may extend inwardly from the inner rim 26 to define a portion of the collection opening 18.

The flow-through portion 14 may be mounted on the body interface element 24 of the body interface portion 12. The flow-through portion 14 defines a passage 40 therethrough that extends between the opposite ends 42, 43 of the flow-through portion. The opposite ends 42, 43 of the portion 14 have respective opposite openings 44, 45, and the flow-through portion 14 may be elongated between the ends 42, 43. The passage 40 is in fluid communication with the collection opening 18 of the body interface portion such that fluid received by the collection opening is able to freely flow into and through the passage.

The flow-through portion 14 may comprise a generally tubular passage element 46 that forms the passage 40, and may include a perimeter wall 50. The perimeter wall 50 may have an upper end portion 52 and a lower end portion 53, and has a diameter. The diameter of the perimeter wall 50 may decrease from the upper end portion 52 to the lower end portion 53 when the perimeter wall is in not mounted on the body interface portion and the exit portion, although in some embodiments the diameter of the wall 50 may be substantially uniform. The perimeter wall 50 may be attached to and extend downwardly from the annular interface element 24, and the upper end portion may be positioned over the interface element. The upper end portion 52 of the wall 50 may be constricted on the interface portion 12 to help secure the perimeter wall to the interface portion, and such constriction may be accomplished, for example, by forming the wall 50 smaller than the interface portion and stretching the material of the perimeter wall to fit over part of the interface portion, or by forming the wall 50 larger than the interface portion and shrinking the wall 50 onto the interface portion. The perimeter wall 50 may be, for example, stretched over the outer perimeter 36 of the outer flange and may extend over at least a portion of the upper flange surface 34 of the outer flange. Preferably, although not critically, the perimeter wall 50 does not cover the upper edge 28 of the raised inner rim 26.

The perimeter wall 50 may be formed of a flexible material that permits manipulation and movement of the position of the exit portion 16 with respect to the body interface portion when the body interface portion is positioned against the body of the user. The perimeter wall 50 may be formed of a flexible elastomeric material, although the elastic character of the perimeter wall is not critical, and the wall 50 may be stretchable at least in the diametric or radial direction, if not also in the longitudinal direction. The elastomeric material may also be resiliently stretchable such that the material substantially recovers its shape when stretched, although this is not critical. In some embodiments, the material may comprise a latex material or a thermo-plastic elastomeric material. The perimeter wall 50 preferably may be collapsible such that the end portions 52, 53 of the perimeter wall 50 may be brought together without damaging the perimeter wall and in a highly compact manner. The perimeter wall may have a relatively thin wall thickness to permit ready collapse of the perimeter wall.

The exit portion 16 forms an exit for urine that is moving through the passage 40 of the flow-through portion 14, and may form a hand hold for a user to grasp to extend the flow-through portion and establish a direction of urine exit from the device through movement of the exit portion independent of the interface portion. The exit portion may define an exit opening 54 for the exiting fluid to flow through, and the exit opening may be relatively constricted in size as compared to the size or diameter of the flow-through portion. The exit portion has a top 56 and a bottom 58, and may be elongated between the top and bottom as compared, for example, to a diameter of the exit portion. The exit portion may be formed of a substantially rigid material which may be substantially inflexible using hand or finger pressure.

The exit portion 16 may comprise an annular exit element 60 that forms the exit opening 54. The exit opening 54 may have various shapes. The exit element 60 may have a maximum dimension which may comprise a length C. The exit element 60 may include an annular upper projection 62 that is positioned adjacent to the top 56 of the exit portion. The upper projection 62 may have a substantially cylindrical inner surface 64 and a generally cylindrical outer surface 65.

The exit element 60 may include an annular lower wall 66 that gradually extends radially inwardly from the upper projection 62 to the exit opening 54, and may have an inverted substantially frusta-conical shape. In some embodiments, a shoulder 70 may be formed between the upper projection and the lower wall. In the most preferred embodiments, the lower wall has an outer periphery that is united to the upper projection such that these elements are formed of a single piece. The upper projection 62 may form an upper opening 68 for the exit element 60 that opens into a channel 69 between the upper opening and the exit opening 54.

The perimeter wall 50 of the flow-through portion 14 may be attached to the annular exit element 60, and the lower end portion 53 may be stretched over (or may be shrunk onto) the outer surface 65 of the upper projection. An edge of the perimeter wall at the lower end portion may abut against the annular shoulder 70 on the lower surface.

Figure 5:
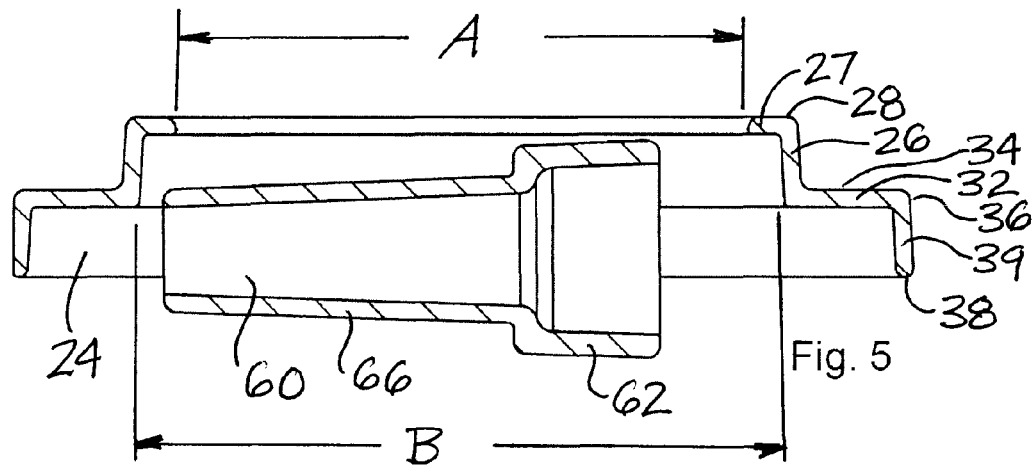
FIG. 5 is a schematic side sectional view of the device shown with the lower exit portion being nested in the upper body interface portion (with the collapsed flow-through portion removed for clarity).
Figure 6:
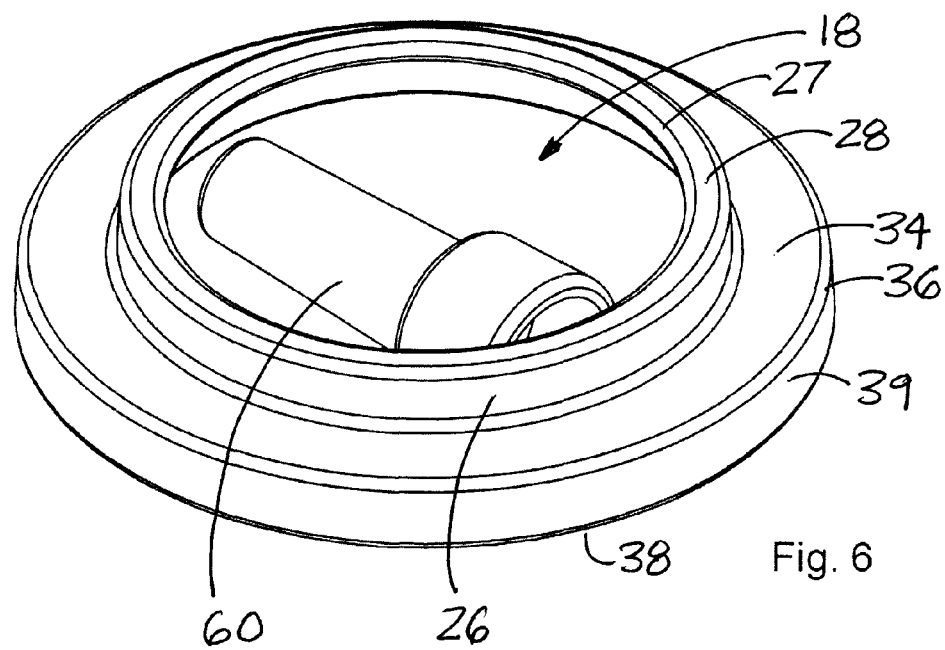
FIG. 6 is a schematic perspective view of the device shown with the lower exit portion being nested in the upper body interface portion.
Figure 7:
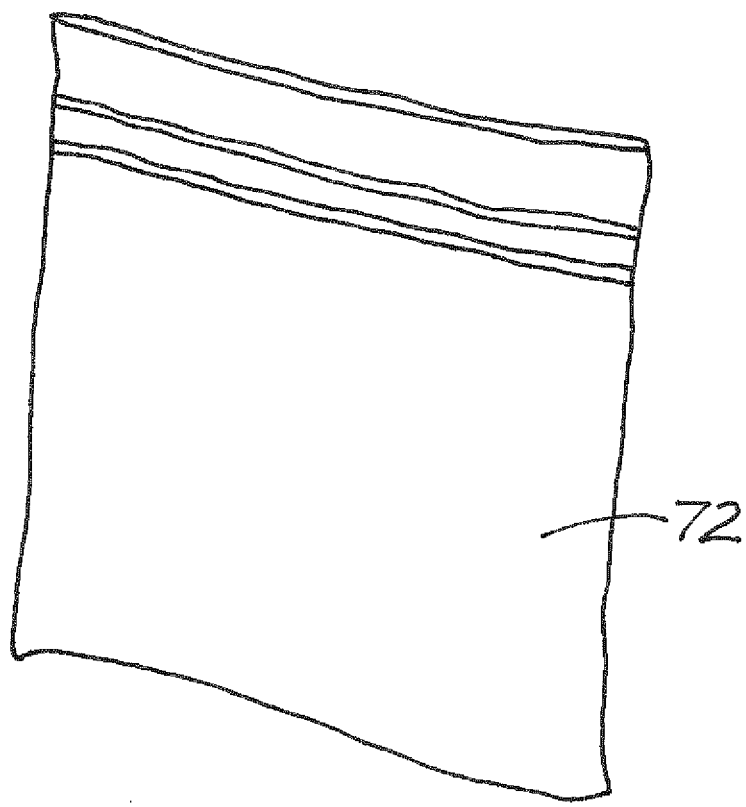
FIG. 7 is a schematic perspective view of an embodiment of a package holding the device.

Significantly, in many preferable embodiments of the device 10 the flow-through portion 14 of the device 10 is substantially fully collapsible so that the exit portion 16 is substantially fully nestable in the body interface portion 12 (see FIGS. 5 and 6). To provide this advantage, the second diameter B of the interface portion may be greater than the length C of the exit portion to permit nesting of the exit portion in the body interface portion. In some further preferred embodiments, the length C of the exit portion is less than the diameter of the collection opening to permit even further nesting of the exit portion in the body interface portion A significant aspect of the device 10 that results in part from the nesting relationship is that the device may be provided in a relatively thin and compact package 72 that may be conveniently and discreetly carried by the user (see FIG. 7). The device 10 is also intended and fabricated to be easily disposed of after a single use of the device in a conventional trash receptacle without occupying a large amount of space therein.

In some embodiments, the body interface portion 12 has a maximum diameter of approximately 3.5 inches or less, and may have a size in the range of approximately 2 inches to approximately 3.5 inches. The diameter of the outer surface 30 of the raised inner rim may have a diameter of approximately 2.5 inches or less in most preferable embodiments, and in some highly suitable embodiments may have a diameter of between approximately 2.5 inches and approximately 1.5 inches. The maximum dimension of the exit element, designated as the second diameter B, may be approximately 2.5 inches of less, and may be between approximately 2.5 inches and approximately 1.5 inches, but suitably should be less than the diameter of the inner annular surface 30, which may correspond to the second diameter B. The dimensions of the device may be reduced or scaled down for smaller or younger persons, such as children, and in some embodiments may be reduced in size by approximately 0.25 inch.

In use, the raised inner rim 26 may be inserted around the lips of the vulva so that the surface of the upper edge 28 of the rim 26 (and the rim extension) contacts the inner skin around the urethra, surrounding the labia majora and labia minora and the upper flange surface 34 of the relatively shallower outer flange 32 may contact the lips, so that the rim 26 isolates the stream of urine. The substantially rigid and inflexible material of the upper body interface portion resists bending when pressed against the body and further facilitates 30 a good seal.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

I claim:

1. A urination assistance device for guiding urine flow from the human body, the device comprising:
   an upper body interface portion defining a collection opening;
   a medial flow-through portion mounted on the body interface element and defining a passage therethrough, the flow-through portion having opposite ends with opposite openings and being elongated between the ends, the passage being in fluid communication with the collection opening of the body interface portion; and
   a lower exit portion mounted on the flow-through portion and defining an exit opening for exit of urine moving through the passage of the flow-through portion for providing a hand hold for a user to grasp to extend the flow-through portion and establish a direction of urine exit from the device;
   wherein one portion selected from the body interface portion and the exit portion is receivable in another portion selected from the body interface portion and the exit portion, with the flow-through portion positioned between the one portion and the another portion;
   wherein the body interface portion and the exit portion are each substantially inflexible and the flow-through portion is flexible.

2. The device of claim 1 wherein the exit portion is substantially fully nestable in the body interface portion with the flow-through portion positioned therebetween.

3. The device of claim 1 wherein at least a portion of the exit portion is capable of being received in the body interface portion with the flow-through portion positioned therebetween.

4. The device of claim 1 wherein the flow-through portion of the device is substantially fully collapsible so that the exit portion is substantially fully nestable in the body interface portion.

5. The device of claim 1 wherein the device is a single use device.

6. A urination assistance device for guiding urine flow from the human body, the device comprising:
- an upper body interface portion defining a collection opening, the body interface portion including an annular interface element having a raised inner rim positioned adjacent to the collection opening, the inner rim being substantially circular in shape, and an outer flange extending radially outwardly from the inner rim and having an upper flange surface depressed with respect to an upper edge surface of the inner rim;
- a medial flow-through portion mounted on the body interface element and defining a passage therethrough, the flow-through portion having opposite ends with opposite openings and being elongated between the ends, the passage being in fluid communication with the collection opening of the body interface portion; and
- a lower exit portion defining an exit opening for exit of urine moving through the passage of the flow-through portion and providing a hand hold for a user to grasp to extend the flow-through portion and establish a direction of urine exit from the device.

7. The device of claim 6 wherein the exit portion is substantially fully nestable in the body interface portion with the flow-through portion positioned therebetween.

8. The device of claim 6 wherein one portion selected from the body interface portion and the exit portion is substantially fully nestable in another portion selected from the body interface portion and the exit portion with the flow-through portion positioned therebetween.

9. The device of claim 6 wherein at least a portion of the exit portion is capable of being received in the body interface portion with the flow-through portion positioned therebetween.

10. The device of claim 6 wherein the body interface portion and the exit portion are each substantially inflexible and the flow-through portion is flexible.

11. The device of claim 6 wherein the flow-through portion of the device is substantially fully collapsible so that the exit portion is substantially fully nestable in the body interface portion.

12. The device of claim 6 wherein the flow-through portion comprises a tubular passage element with a perimeter wall, an upper end portion of the perimeter wall being stretched about a portion of the body interface portion and a lower end portion being stretched about the exit portion.

13. The device of claim 6 wherein the flow-through portion comprises a tubular passage element with a perimeter wall, and the perimeter wall is formed of an elastomeric material.

14. The device of claim 6 wherein the exit opening has an elongated shape.

15. A urination assistance device for guiding urine flow from the human body, the device comprising:
- an upper body interface portion defining a collection opening, the body interface portion including an annular interface element having a raised inner rim positioned adjacent to the collection opening, the inner rim being substantially circular in shape, and an outer flange extending radially outwardly from the inner rim and having an upper flange surface depressed with respect to an upper edge surface of the inner rim;
- a medial flow-through portion mounted on the body interface element and defining a passage therethrough, the flow-through portion having opposite ends with opposite openings and being elongated between the ends, the passage being in fluid communication with the collection opening of the body interface portion; and
- a lower exit portion defining an exit opening for exit of urine moving through the passage of the flow-through portion and providing a hand hold for a user to grasp to extend the flow-through portion and establish a direction of urine exit from the device;
- wherein the flow-through portion is flexible to permit the exit portion to move into the collection opening of the body interface portion.

16. The device of claim 15 wherein the body interface portion and the exit portion are each substantially inflexible.

17. The device of claim 15 wherein the exit portion is substantially fully nestable in the body interface portion with the flow-through portion positioned therebetween.

18. The device of claim 15 wherein at least a portion of the exit portion is capable of being received in the body interface portion with the flow-through portion positioned therebetween.

19. The device of claim 15 wherein the flow-through portion of the device is substantially fully collapsible so that the exit portion is substantially fully nestable in the body interface portion.

20. The device of claim 15 wherein the device is a single use device.

* * * * *